US006405076B1

(12) United States Patent
Taylor et al.

(10) Patent No.: US 6,405,076 B1
(45) Date of Patent: Jun. 11, 2002

(54) ARTIFACT REJECTOR FOR REPETITIVE PHYSIOLOGIC-EVENT-SIGNAL DATA

(75) Inventors: Lee A. Taylor, Portland; Ronald G. Bennett, Gladstone; Thomas J. Dorsett, Hillsboro, all of OR (US)

(73) Assignee: Protocol Systems, Inc., Beaverton, OR (US)

( * ) Notice: Subject to any disclaimer, the term of this patent is extended or adjusted under 35 U.S.C. 154(b) by 0 days.

(21) Appl. No.: 09/364,272

(22) Filed: Jul. 29, 1999

Related U.S. Application Data

(63) Continuation of application No. 08/721,721, filed on Sep. 20, 1996, now abandoned.
(60) Provisional application No. 60/004,039, filed on Sep. 20, 1995.

(51) Int. Cl.[7] .................................................. A61B 5/02
(52) U.S. Cl. ........................ 600/513; 600/493; 128/901
(58) Field of Search ........................ 128/901; 600/485, 600/493–496, 500, 490, 513

(56) References Cited

U.S. PATENT DOCUMENTS

| | | | | |
|---|---|---|---|---|
| 4,960,126 A | * | 10/1990 | Conlon et al. | ............... 128/700 |
| 4,986,277 A | * | 1/1991 | Sackner | ...................... 128/672 |
| 5,337,750 A | * | 8/1994 | Walloch | ...................... 128/681 |
| 5,392,781 A | | 2/1995 | Phillips et al. | |

* cited by examiner

Primary Examiner—George R. Evanisko

(74) Attorney, Agent, or Firm—Kolisch Hartwell Dickinson McCormack & Heuser

(57) ABSTRACT

An artifact rejector for repetitive physiologic-event-signal data generated from electronically-controlled physiologic-event-measuring equipment includes a physiologic-event-signal averager in communication with such physiologic-event-measuring equipment. The artifact rejector is constructed to generate and store repetitive averaged physiologic-event-signal data based upon a substantially stable time relationship between corresponding physiologic-event-signal data and heart-beat-related-signal data. The repetitive averaged physiologic-event-signal data includes less noise than the repetitive physiologic-event-signal data. The artifact rejector generates and continuously updates an averaged-data template by storing such repetitive averaged physiologic-event-signal data for a preselected number of measured physiologic events. The artifact rejector also includes a physiologic-event-noise estimator and a physiologic-event-noise monitor in communication with such physiologic-event-measuring equipment, and capable of instructing the monitor to adjust the measurement cycle based upon estimated, monitored noise. The averager preferably includes a sharp roll-off, low pass filter and examples include a fourth-order Bessel filter, two cascaded, identical second-order Bessel filters, an elliptic filter, a Tchetscheby-scheff filter, or finite impulse response filters. The heart-beat-related signal is preferably an ECG signal. A method of artifact rejection includes generating and storing repetitive averaged physiologic-event-signal data based upon a substantially stable time relationship between corresponding physiologic-event-signal data and heart-beat-related-signal data, with the repetitive averaged physiologic-event-signal data including less noise than the repetitive physiologic-event-signal data.

5 Claims, 6 Drawing Sheets

ARTIFACT REJECTOR FOR REPETITIVE PHYSIOLOGIC-EVENT-SIGNAL DATA

CROSS-REFERENCE TO RELATED APPLICATIONS

This application is a continuation of U.S. patent application Ser. No. 08/721,721 entitled "ARTIFACT REJECTOR FOR REPETITIVE PHYSIOLOGIC-EVENT-SIGNAL DATA" filed on Sep. 20, 1996, now abandonded which application claims priority from U.S. Provisional Patent Application Serial No. 60/004,039 entitled "ARTIFACT REJECTOR FOR REPETITIVE PHYSIOLOGIC-EVENT-SIGNAL DATA" filed on Sep. 20, 1995.

BACKGROUND AND SUMMARY OF THE INVENTION

The present invention relates to artifact rejection using signal-noise averaging and filtering techniques, and more particularly to averaging repetitive signals representative of repetitive noise-vulnerable physiologic events such as blood pressure pulses based upon substantially noise-immune heart-beat-related events such as ECG data or plethysmograph data from a pulse oximeter.

Ensemble-signal averaging (ESA) is known generally as a technique for removing severe noise from a repetitive input signal based upon the existence of a timing source that is substantially immune to noise. In the field of medical monitoring, such a technique is used in connection with measuring brain stem auditory evoked response, and with measuring ECG late potentials. Essentially, the idea is that noise will occur randomly with respect to the timing source, and will cancel out through such averaging if sufficient data is taken. In contrast, desired measured data, such as medical monitoring data, will not be random with respect to the timing source. Therefore, medical monitoring data will not cancel out through averaging, regardless of the amount of data points taken for averaging purposes.

Another type of medical monitoring involves the oscillometric method of noninvasive blood pressure (NIBP) measurement. Various methods of dealing with artifact have been proposed including those described in U.S. Pat. Nos. 4,949,710 to Dorsett et al. and 5,339,822 to Taylor et al. Generally speaking, conventional artifact rejection methods for measured physiologic pulsatile data focus on determinations for accepting or rejecting data corresponding to a given pulse. In other words, conventional methods focus on analyzing data, pulse-by-pulse, to learn whether to accept or reject.

However, until now, there has been no proposal for dealing with artifact in the form of relatively severe noise that is superimposed on NIBP oscillometric pulses in the oscillometric channel of an NIBP monitor. For purposes of the to-be-described invention, that relatively severe noise is not in synch with a to-be-described reference signal like an ECG signal. As will be understood, the to-be-described artifact rejector and artifact rejection method of the invention relies on the unwanted artifact/noise to be different in fundamental frequency and harmonics from the reference signal and its harmonics. In the context of oscillometric NIBP, it does not take much to result in severe noise because in ideal circumstances the largest oscillometric pulses are about 7–8-mmHg, and often such pulses are less than 1-mmHg. Environmental conditions that can produce severe noise in the context of oscillometric NIBP include actions that impact the blood pressure cuff such as patient motion, vehicular vibration (where the patient is being transported), and inadvertant physical contact between the patient and the health care professional(s) operating the monitor or treating the patient.

Also until now, ESA has never been tried on oscillometric NIBP because NIBP is not a method that can accept substantial extensions of cycle time due to patient discomfort associated with the occluding cuff. ESA has also not been tried on oscillometric NIBP because it could easily distort the shape of the clinically useful graphical information corresponding to a plot of pulse size (amplitude) vs. cuff pressure during an NIBP-measurement cycle (also called the NIBP cycle envelope).

Accordingly, it is a principal object of the present invention to provide an artifact-rejection mechanism which overcomes the drawbacks of prior-art proposals.

Another object is to provide such a mechanism which can be used to reject artifact causing severe noise in oscillometric NIBP.

Yet another object is to provide such a mechanism that allows for application of ESA to reject artifact in oscillometric NIBP.

A further object is to provide such a mechanism that is usable in oscillometric NIBP and preserves the shape of the NIBP cycle envelope.

Another object is to provide such a mechanism that will not substantially extend NIBP cycle time.

A still further object is to provide such a mechanism that will optimize NIBP cycle time.

Yet another object is to provide such a mechanism that will account for unusual time relationships that can occur between heart-beat related signal data such as ECG-signal data and oscillometric-pulse-signal data.

Another object is to provide such a mechanism that will determine when data that has been averaged has been adequately initialized.

In brief summary, one aspect of the invention is an artifact rejector for repetitive physiologic-event-signal data generated from physiologic-event-measuring equipment that includes a physiologic-event-signal averager in communication with such equipment. The artifact rejector of the invention is constructed to generate and store repetitive averaged physiologic-event-signal data based upon a substantially stable time relationship between corresponding physiologic-event-signal data and heart-beat-related-signal data, with the repetitive averaged physiologic-event-signal data including less noise than the repetitive physiologic-event-signal data. The artifact rejector generates and continuously updates an averaged-data template by storing such repetitive averaged physiologic-event-signal data for a preselected number of measured physiologic events. The averager preferably includes a sharp roll-off, low pass filter, and examples include a fourth-order Bessel filter, two cascaded, identical second-order Bessel filters, an elliptic filter, a Tchetschebyscheff filter, or finite impulse response filters. The heart-beat-related signal is preferably an ECG signal.

Another aspect of the present invention is a method of artifact rejection that includes averaging such repetitive physiologic-event-signal data based upon a substantially stable time relationship between corresponding physiologic-event-signal data and heart-beat-related-signal data, with the repetitive averaged physiologic-event-signal data including less noise than the repetitive physiologic-event-signal data.

These and other objects and advantages of the invention will be more clearly understood from a consideration of the accompanying drawings and the following description of the preferred embodiment.

Figure 1:
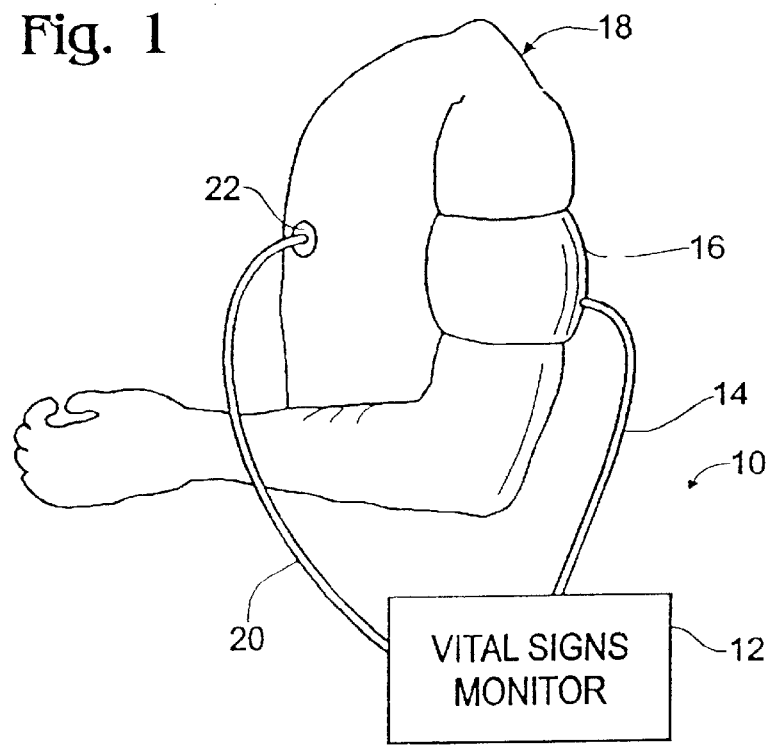
FIG. 1 is a partial view of a living subject having certain vital signs being monitored with vital signs monitoring apparatus (shown in schematic block diagram) suitable for practicing the method of the present invention.

DETAILED DESCRIPTION OF THE PREFERRED EMBODIMENT AND THE PREFERRED MANNER OF PRACTICING THE INVENTION

In addition to the following description, the present application also includes attachment A which is a source code listing for the artifact rejector of the present invention. That listing identifies the artifact rejector in its preferred embodiment as a software module that is included in other desired software modules of physiologic-event-measuring equipment which equipment is preferably an electronically-controlled vital signs monitor. The artifact rejector software module of the invention may be set up to read directly the output of measured repetitive physiologic-signal data, or preferably (see further in attachment A) the artifact rejector software module may be set up to read a modified output such as one in which a match filter is used to remove DC current effects from the signal data.

Attachment B includes a combination of text and graphics to describe further the background of the invention, and a description of the invention and how preferably to implement it.

Before describing the invention, certain other matters should be understood. First, the invention could be used as an artifact rejector for any repetitive physiologic-event-signal data generated from physiologic-event-measuring equipment (preferably electronically controlled) that also measures heart-beat-related-signal data. However, for purposes of this description, the invention will be described in the context of an artifact rejector for oscillometric NIBP.

Second, the present disclosure incorporates by reference the teachings of U.S. Pat. Nos. 4,949,710 to Dorsett et al. and 5,339,822 to Taylor et al.

With respect to the type of oscillometric NIBP usable with the invention, any conventional type is suitable including NIBP that uses stepwise deflation of an occluding cuff, or NIBP that uses gradual deflation of the occluding cuff. Use with gradual deflation of the occluding cuff is preferred and an example of such gradual deflation is commercially available in the PROPAQ ENCORE vital signs monitor manufactured by Protocol Systems Inc. of Beaverton, Oreg. The gradual deflation is accomplished by using a suitable software state module to control cuff inflation, deflation and final determination of blood pressure parameters. In other words, there is a continuous bleed NIBP, and it is accomplished with a proportional flow valve (PFV) and a bleed valve positioned between the occluding cuff and pump, with pressure transducers positioned between the cuff and PFV, and a bleed valve in parallel with the pump. Another name for a PFV is a linear valve, a continuously adjustable proportional control valve, or an infinitesimally adjustable proportional control valve.

Benefits of this topology include NIBP measurements that can be made during smooth, continuous (non-stepped) inflation and/or deflation. The time profile of the deflation can be exponential. Exponential deflation is preferred because it optimizes patient comfort by limiting measurement time at relatively high cuff pressures. Another reason is that exponential deflation affords obtaining an effective amount of signal data at the low-pressure-side of the oscillometric curve because the slope of that curve is greater at the lower pressures than it is at the higher pressures.

Before beginning the description with a review of the drawings, it is important to understand that the invention is focused on validating pulsatile (pulse-like) physiologic events, such as oscillometric pulses carrying blood-pressure information. The to-be-described steps of the invention may be practiced by writing them into computer programs that may be stored in the memory of control/processing circuitry of otherwise conventional vital signs monitoring apparatus. As was mentioned above, the following description will relate to monitoring and validating blood-pressure information in the form of oscillometric pulses, with the understanding that various other kinds of heartbeat-induced physiologic events can be handled in the practice of the invention.

Referring now to FIG. 1, the to-be-described artifact rejector of the invention resides as a software module in vital signs monitoring apparatus shown at 10 with a monitor 12 and a conduit 14 coupled to an occluding cuff 16 that is fitted around an arm of a living subject 18. Conductive cable structure 20 interconnects monitor 12 with an ECG lead 22. Any ECG-lead arrangement may be used.

However, it is presently proposed to modify a cuff like cuff 16 by forming or locating two of the three required ECG electrodes on the inside surface of the cuff. That novel, modified cuff would simplify the number of electrodes that must be attached to the patient, leaving the need for attaching only one other electrode to the patient.

Continuing with FIG. 1, monitor 12 is a microprocessor-controlled device that includes the usual pump, (for cuff 16, and not shown herein) and sensors/transducers (for cuff 16 and ECG lead 22, also not shown herein). Apparatus 10 also includes the usual integrated circuitry for controlling the monitor, for converting analog-signal-data (fed from cuff 16 and lead 22) to digital-signal-data, and for processing the digital-signal-data to determine vital signs parameters. As known to those skilled in the art, such circuitry includes a microprocessor, RAM for acquiring data, and ROM for storing computer programs that direct the microprocessor to control the monitor and to process data.

Also as is known to those skilled in the art, apparatus 10 is usable to measure a subject's blood pressure and heart rate during a suitable measurement cycle. For practicing the present invention, the usual NIBP-cycle may be used as a measurement cycle in the practice of the present invention. Such cycle includes monitoring and processing pressure-signal information from cuff 16 for a defined range of pulsatile information, i.e. from a supra-systolic pressure (cuff inflated) to below diastolic pressure (cuff deflated preferably gradually). Gradual cuff deflation is preferred because it optimizes patient comfort and promotes accuracy of data measurement because, in stepwise cuff deflation, data occuring during step deflation can be lost.

During a measurement cycle, conduit 14 will convey analog-signal-data in what may be thought of as a stream of pulsatile information (also referred to as oscillometric pressure data) and cable structure 20 will convey what may be thought of as a stream of QRS complexes. Such stream of QRS complexes will be referred to herein as an R-wave stream. For a detailed description of an NIBP-cycle, one may look to U.S. Pat. No. 4,889,133 to Nelson et al., which patent is incorporated herein by reference. For purposes of the present invention, a key feature of the R-wave stream is that its occurrence has a substantially stable time relationship with the occurrence of oscillometric pressure data. That relationship forms the basis for performing to-be-described signal averaging on oscillometric pressure data as a way of removing artifact.

Figure 2:
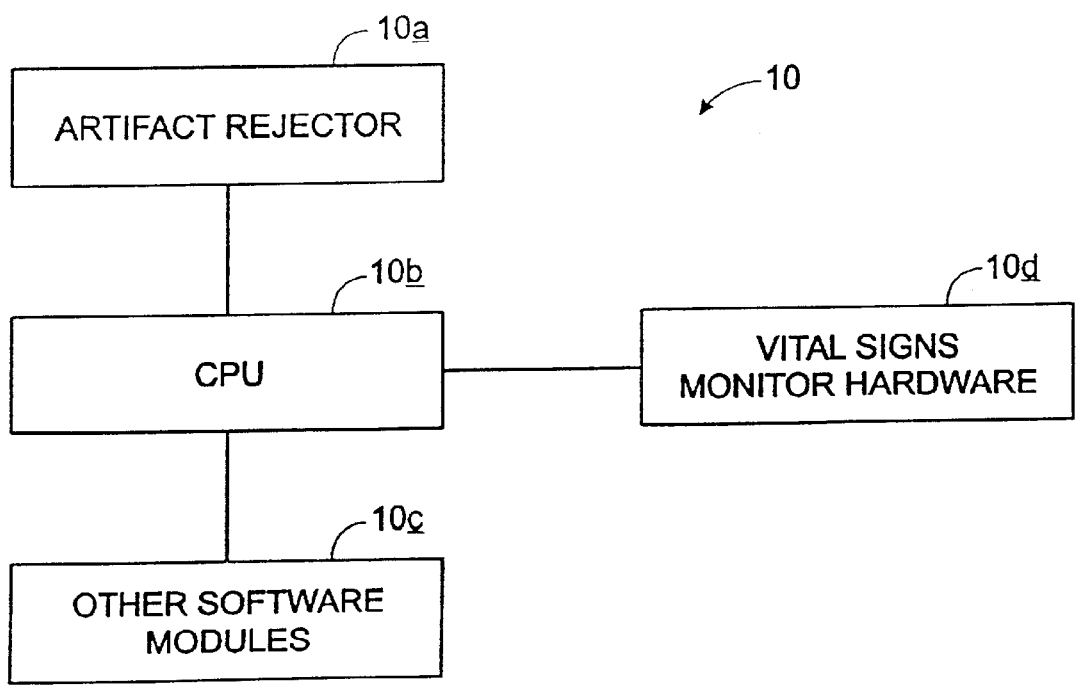
FIG. 2 is a schematic block diagram of vital signs monitoring apparatus including the artifact rejector of the invention.

Referring to FIG. 2, a schematic block diagram of vital signs monitoring apparatus 10 is shown to illustrate schematically how artifact rejector 10a of the invention resides in apparatus 10. In the context of FIG. 2, apparatus 10 can be thought of as including artifact rejector 10a, a software module that communicates with CPU 10b. Other conventional software modules 10c are included in apparatus 10, as are conventional vital signs monitor hardware 10d. Referring back to FIG. 1, examples of that hardware are cuff 16 and conduit 14, and ECG lead 22 and conductive cable structure 20.

Figure 8:
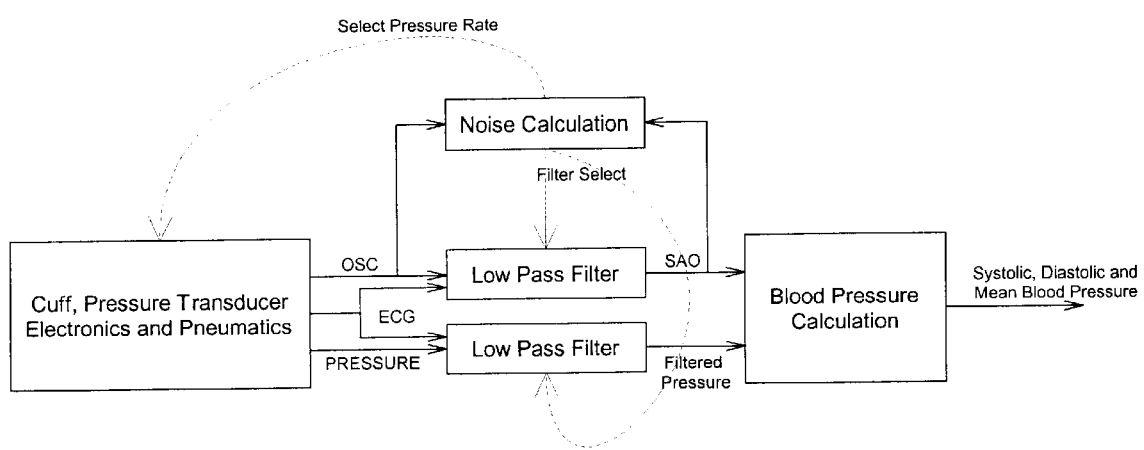
FIG. 8 is a graphical illustration of a typical NIBP-measurement cycle using NIBP-measurement equipment described in the Detailed Description.

Next, reference is made to FIG. 8 and the following Table 1:

FIG. 8

First referring to FIG. 8, there is shown from left to right the sequence of measuring NIBP parameters after reaching a suprasystolic pressure on a patient by using equipment such as the PROPAQ ENCORE which includes a suitable system of a blood pressure cuff, pressure transducer(s), and electronic and pneumatic control equipment. As is known, two streams (or channels) of pressure information (i.e. signal data) are produced during an NIBP measurement cycle and those correspond to oscillometric pressure data (OSC in FIG. 8) and cuff counterpressure data (PRESSURE in FIG. 8). In addition, FIG. 8 indicates that ECG data (an R-wave data stream) is present with each stream of pressure data to provide the necessary heart-beat-related signal data for use in accordance with the invention.

Referring to the middle of FIG. 8, each pair of data streams (the OSC/ECG(R-wave stream) and the PRESSURE/ECG are passed through a suitable low pass filter, and the oputput from each filter is used to determine blood pressure parameters such as systolic, diastolic and mean arterial pressure (MAP). As used herein, filtering of data means to take an input signal carrying data, and perform preselected mathematical operations on that data to produce filtered data. The specific type of filtering presently contemplated by the invention involves removing noise (also referred to as artifact) from the data. The filtering of the PRESSURE/ECG data can be done using any suitable filter.

The filtering of the OSC/ECG data is to be performed using one of the above-identified filters and the above-described ESA technique, and the output data is referred to in FIG. 8 as SAO, or signal-averaged oscillometric. Referring back to FIG. 2, artifact rejector 10a generates and stores SAO which may also be thought of as repetitive averaged NIBP-signal data. Presently, it has been found effective to measure and store SAO for oscillometric pressure signal data occuring for 1 second after the occurrence of the occurrence of an R-wave. As shown below, the SAO output has less noise associated with it than the OSC/ECG data that is input to the filter.

Referring again to the middle of FIG. 8, the usual noise calculation is performed on the OSC/ECG data stream. That noise calculation is also performed on the SAO. Based upon the noise calculation, two adjustments are made to the NIBP measurement as indicated by the dashed lines with arrows. Pressure rate is adjusted by selecting a next pressure rate gradually to lower cuff counterpressure during the NIBP measurement cycle, and that pressure rate may also be thought of as the NIBP measurement cycle rate or bleed rate (referring to the rate at which cuff counterpressure is decreased). Based upon the next pressure rate, the filter is also adjusted.

Table 1 shows the criteria for making the above two adjustments:

TABLE 1

| Noise (Pulse I)/mae | Noise (Pulse II)/mae | Filter/ cycls./smpls. <HR K | Filter/ cycls./smpls. >HR K | Bleed Rate/% ΔP/pulse |
|---|---|---|---|---|
| <75 | <150 | 0.065 | 0.039 | 3.3 |
| 75–125 | 150–250 | 0.039 | 0.039 | 1.65 |
| 125–250 | 250–500 | 0.027 | 0.027 | 1.1 |
| 250–400 | 500–800 | 0.017 | 0.027 | 0.825 |
| >400 | >800 | 0.017 | 0.017 | 0 |

Noise units are given in mae, or mean absolute error, filter units are in cycles/sample (with sample referring to signal-data sample), HR K refers to an experimentally determined heart rate of 128 beats/minute, and bleed rate is given as % change in pressure based upon the previous pulse. In other words, if the cuff counterpressure for the previous pulse was 100 mm Hg, then a 3.3 bleed rate means to decrease cuff counterpressure by 3.3% of 100, i.e. to decrease cuff counterpressure to 96.7 mmHg.

Possible noise calculations are shown in the two left columns. Those columns show anticipated noise ranges for two different types of pressure pulses encountered during NIBP measurement (a small one. i.e. Pulse I, and a large one, i.e. Pulse II). Those ranges have been experimentally determined, and have been found useful because desired filter adjustment may vary depending on the type of pulse (see first row of Table 1, compare filter adjustment for pulse I noise <75 mae vs. filter adjustment for pulse II noise <150 mae.

Figure 3:
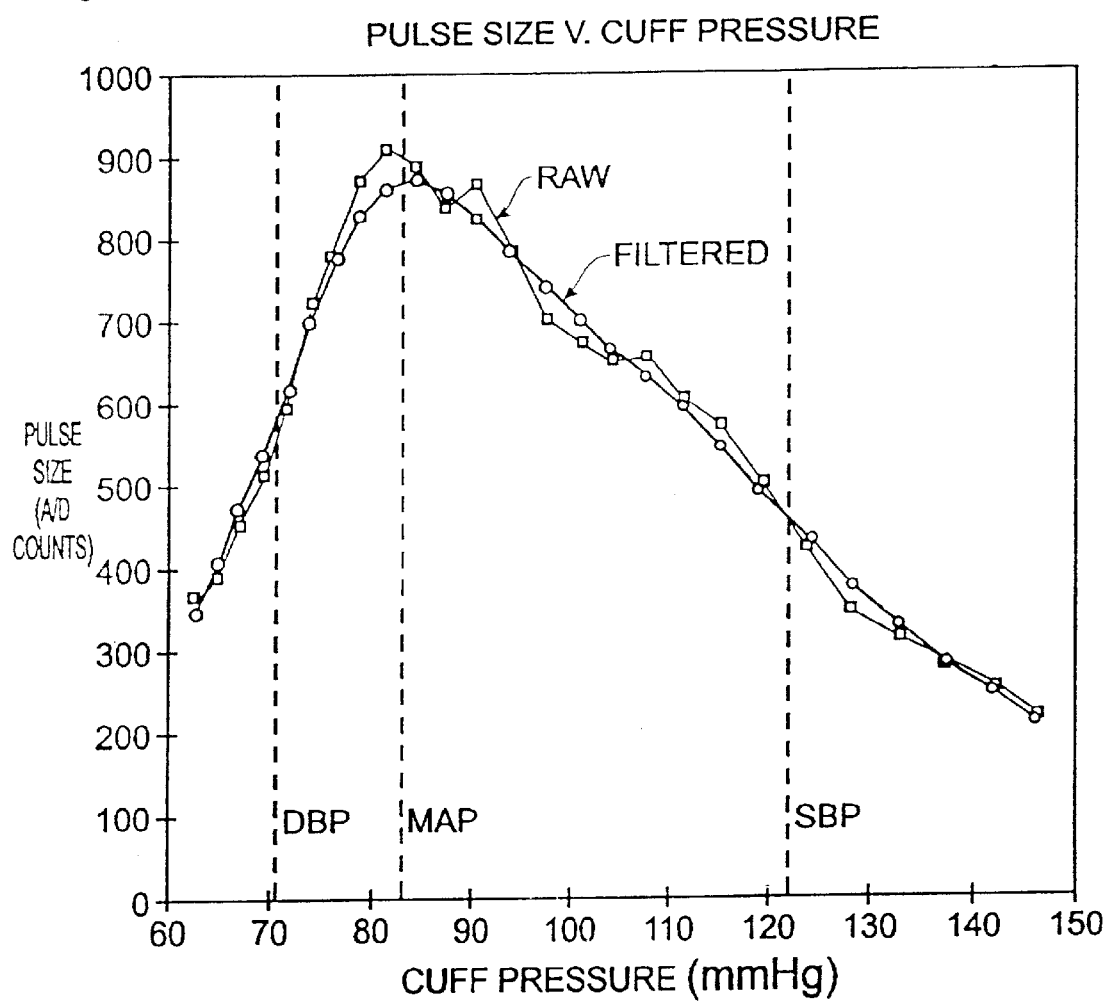
FIG. 3 is a graph of cuff pressure vs. pulse size for a typical NIBP envelope showing the clinically positive correlation between raw (i.e. unfiltered) NIBP-oscillometric-signal data and NIBP-oscillometric-signal data that is averaged using the artifact rejector of the invention.

Referring to FIG. 3, there is a graphical illustration of a NIBP envelope showing the clinically positive correlation between the raw (i.e. unfiltered) NIBP-oscillometric-signal data and the filtered (i.e. averaged using the above-described types of sharp roll-off, low pass filters such as a fourth order Bessel filter, or two cascaded, identical second order Bessel filters ) NIBP-oscillometric-signal data. The filtered data in FIG. 3 was taken from a sharp roll-off, low pass filter composed of two cascaded, identical second order Bessel filters.

Figure 4:
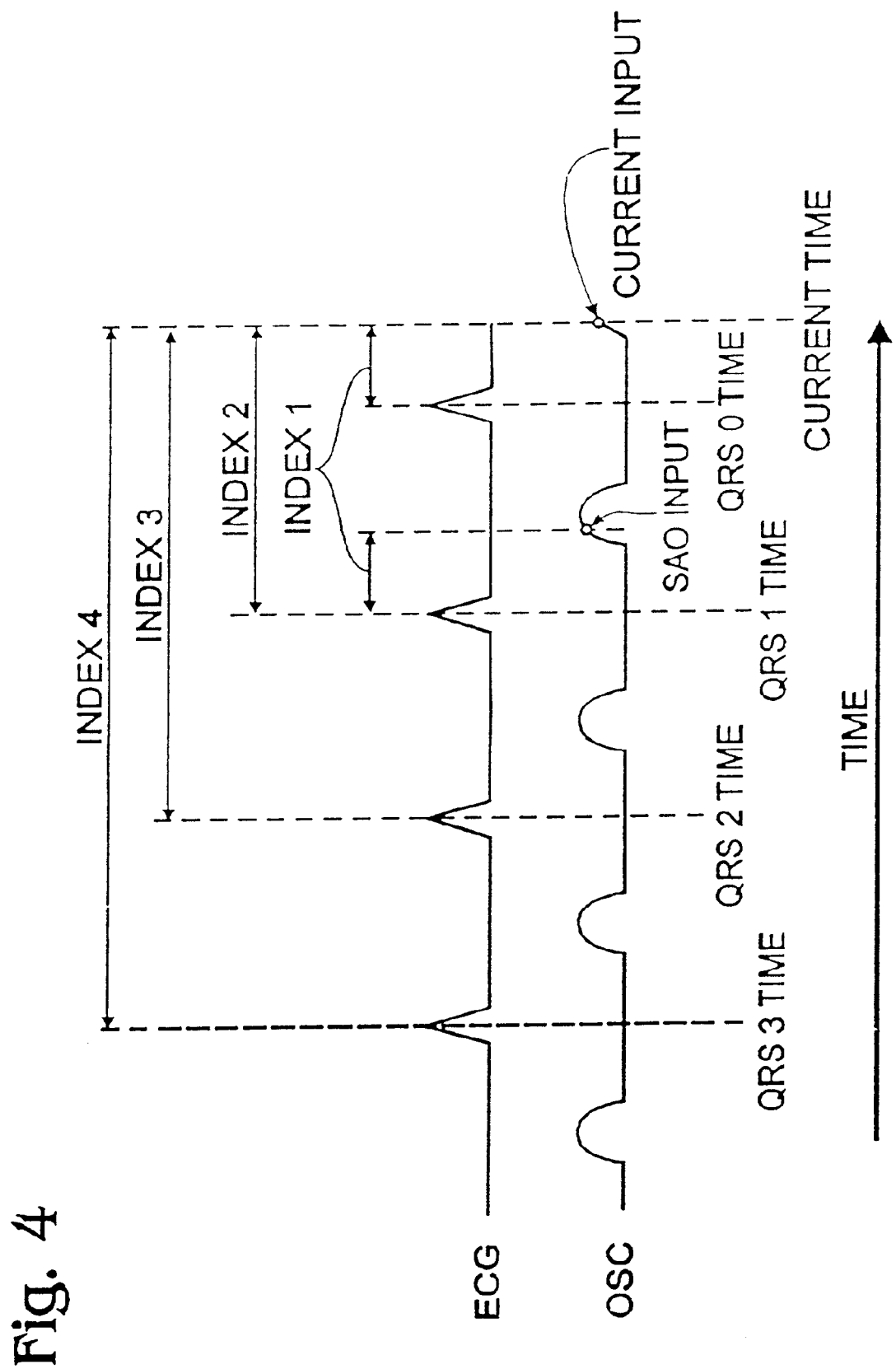
FIG. 4 is a graphical illustration of nomenclature used in the source code listing of the artifact rejector software module.

Referring to FIG. 4, there is a graphical illustration of nomenclature used in the source code listing (attachment A)

of the artifact rejector software module. That nomenclature is used to identify how the module deals with uncertain time delays between a given R-wave and a resulting blood pressure pulse.

Figure 5:
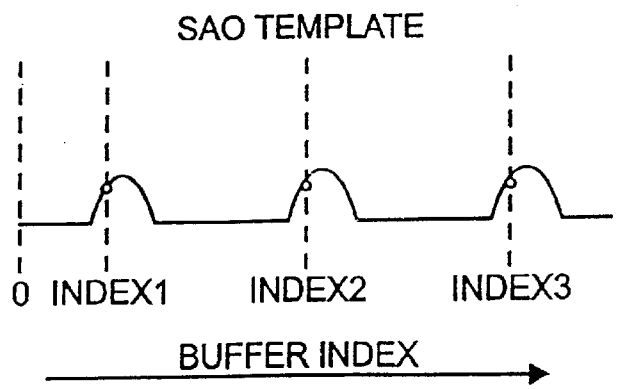
FIG. 5 is a graphical illustration of how a buffer table of averaged NIBP-oscillometric-signal data is updated continuously during an NIBP measurement cycle.

Referring to FIG. 5, there is a graphical illustration of how the buffer table of averaged NIBP-oscillometric-signal data is updated continuously during an NIBP measurement cycle.

Figure 6:
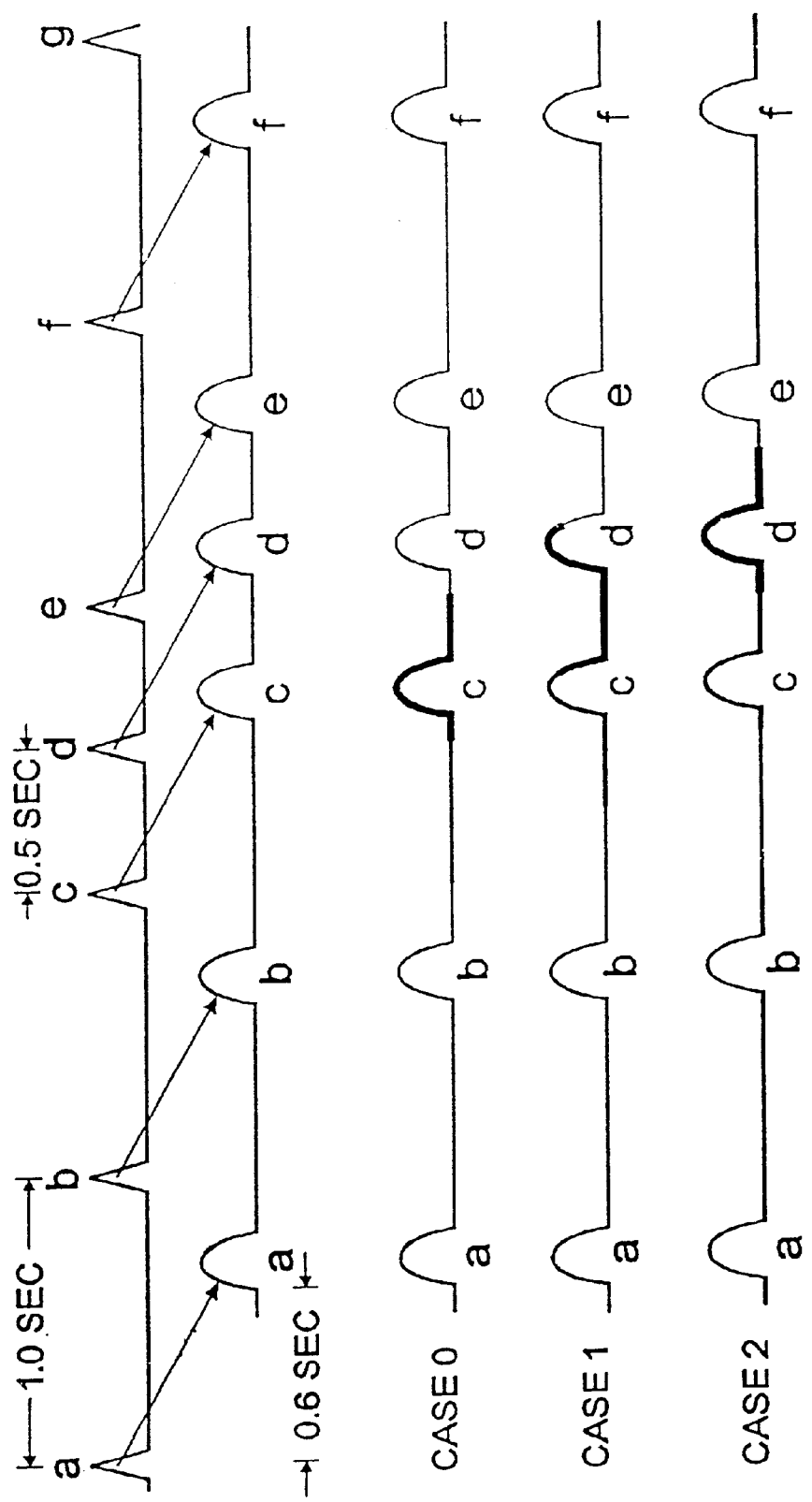
FIG. 6 is a graphical illustration of how the indexing shown in FIG. 4 allows the artifact rejector to detect a relatively long time period between an R-wave and corresponding NIBP-oscillometric pulse (see also attachment B).

Referring to FIG. 6, there is a graphical illustration of how the indexing shown in FIG. 4 allows the artifact rejector to detect a long R-wave to NIBP-oscillometric pulse (see also attachment B).

Figure 7:
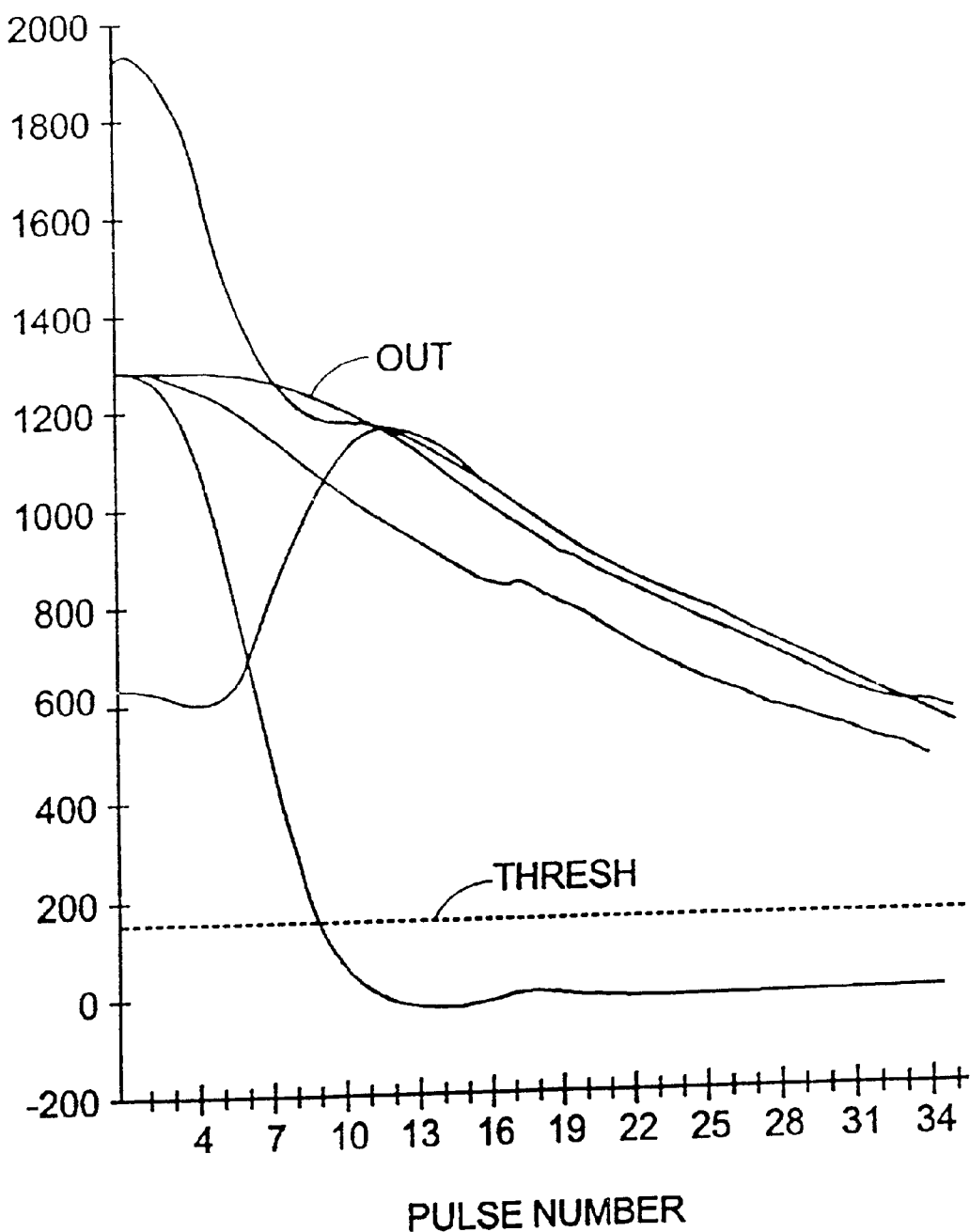
FIG. 7 is a graphical illustration and textual description of how the artifact rejector of the invention runs a time constant experiment to determine when filtered (averaged) NIBP-oscillometric-signal data is initialized sufficiently to accept the data for NIBP measurement.

Referring to FIG. 7, there is a graphical illustration and textual description of how the artifact rejector of the invention runs a time constant experiment to determine when filtered (averaged) NIBP-oscillometric-signal data is initialized sufficiently to accept the data for NIBP measurement.

While the present invention has been shown and described with reference to the foregoing preferred embodiment, it will be apparent to those skilled in the art that other changes in form and detail may be made therein without departing from the spirit and scope of the invention as described further below. Where preselected thresholds are recited generally in the following claims, specific examples of such thresholds are shown in Table 1 and the source code listing in attachment A.

Yet another way to describe the invention is to think of it as an application of ensemble signal averaging (ESA) to the problem of motion artifact reduction in the oscillometric non-invasive blood pressure (NIBP) signal. The algorithm or software module described addresses the problems of preserving the cuff pressure (CP) vs pulse size envelope shape, dealing with the case of a long pulse delay (relative to the QRS wave of the corresponding ECG signal), using limited CPU resources, and optimizing the determination cycle time.

ESA is a known technique to eliminate zero mean noise from repetitive, slowly changing signals with low signal-to-noise ratios. Classic examples are auditory brainstem evoked response signals, and ECG late potentials. The oscillometric NIBP signal is frequently contaminated by severe noise due to patient motion or extraneous bumping of the cuff, especially during vehicular patient transport. Since NIBP systems are often a component of a multi-parameter vital signs monitor, the availability of a synchronizing source, such as the ECG raises the question: Can ESA be applied to NIBP? Indeed, the ECG signal has been used to reject artifact pulses based on R-wave gating. Unlike other signals for which ESA has been used however, the NIBP oscillometric waveform is a signal that changes dynamically with CP, and further, CP must be varied over a short period of time for patient comfort and safety. Thus classical ESA techniques teach away from application to NIBP because classical ESA would require numerous pulses at each pressure level, an impractical requirement for oscillometric NIBP.

With the above in mind, the invented artifact rejector software module for a vital signs monitor removes severe noise from oscillometric signals using signal averaging techniques without lengthening NIBP cycle time beyond practical limitations. The invented artifact rejector also deals with the limited computational capacity of the CPU of the host device, preferably the PROPAQ or PROPAQ ENCORE vital signs monitors manufactured by Protocol Systems Inc. of Beaverton, Oreg.

The artifact rejector of the invention has overcome four obstacles:

Signal averaging of both the cuff pressure and the oscillometric signal are performed in such a manner that the resulting pulse energy vs cuff pressure envelope is not substantially distorted, and is clinically useful.

In some cases, the delay between the ECG R-wave and the resulting oscillometric pulse might exceed one R-to-R interval. This could occur with a high heart rate, low blood pressure and cuff placed on the ankle of a tall, polycythemic subject. The invention analyzes signal data and adapts to deal with such delays.

The filter chosen to perform the point-for-point filtering consumes a minimal proportion of available CPU capacity.

To optimize cycle time, the invention estimates the severity of noise present, and cuff bleed rate and filter pass bandwidth are varied dynamically during measurement, i.e. on the fly.

The invention includes use of a 4th-order Bessel filter. It was found empirically, that this filter had a sufficiently steep rolloff to both retain the passband of the pulse energy vs. cuff pressure envelope and reject typical oscillometric noise. To optimize cycle time, four such Bessel filters were implemented and matched to four exponential bleed rates. The bleed rates varied from 0.82 to 3.3% of cuff pressure per R-to-R interval (see attachment A).

The uncertain R-wave-to-pulse-delay problem was solved by maintaining the composite oscillometric pulse in a one second buffer and continuing to perform signal averaging for each R-wave for up to one second or three R-to-R intervals, whichever occurred first. Thus at heart rates above 60 bpm, it is possible that the one second buffer could contain more than one composite signal averaged pulse. In the case where the R-to-R interval is a very regular (unlikely) the pulses would have the same amplitude, and it would not matter which one the algorithm chooses to use. In the case where there is some R-to-R variation, the true pulse will be the largest one.

Signal noise is estimated by comparing the real-time incoming signal with the composite signal averaged pulse. When noise is low the bleed rate can be set to the highest rate. With increasing noise, a slower bleed rate and a lower corner frequency filter is used. In extremely severe noise, the cuff pressure is held constant and signal ignored for up to ten seconds.

The invention has been successfully implemented on a target platform. FIG. A (next page) illustrates the ability of the invention to remove unwanted noise from a severely corrupted input signal. (This signal was created by performing handwriting during an NIBP determination. The resulting continuous activity of the muscles under the cuff generates noise generally worse than that encountered during patient vehicular transport.) FIG. B (next page) illustrates the resulting pulse energy vs cuff pressure envelope. Note that the horizontal spacing between pulses changes at the points marked "A" and "B". These times correspond to points in time when the cuff bleed rate and filter were changed. The reading collected a total of 61 pulses. The heart rate was 59 and the total cycle time was 67 sec. The blood pressure obtained in this example was 114/73 with a MAP of 86 mmHg. The previous reading, without noise on the same subject was 112/75 with a MAP of 86 mmHg. The invention offers superior performance in transport and hospital environments, and in cases of substantial pulse-to-pulse variation such as atrial fibrillation.

The present invention shows that it is feasible to apply signal averaging to the oscillometric NIBP waveform. The artifact rejector software module of the invention offers superior noise immunity compared to conventional artifact-rejection techniques.

The invention may also be described by the following paragraphs:

1. An artifact rejector for repetitive physiologic-event-signal data generated from physiologic-event-measuring equipment, which equipment also generates repetitive heart-beat-related-signal data during a physiologic-event measurement cycle, comprising:
    a physiologic-event-signal averager in communication with such physiologic-event-measuring equipment, and constructed to generate and store repetitive averaged physiologic-event-signal data based upon a time relationship between corresponding physiologic-event-signal data and heart-beat-related-signal data, with the repetitive averaged physiologic-event-signal data including less noise than the repetitive physiologic-event-signal data.
2. The artifact rejector of paragraph 1, wherein the physiologic-event-signal averager is constructed to generate and continuously update an averaged-data template by storing such repetitive averaged physiologic-event-signal data monitored in a preselected time interval after an occurrence of the heart-beat-related signal.
3. The artifact rejector of paragraph 2, further including a physiologic-event-noise estimator in communication with such physiologic-event-measuring equipment, and constructed to estimate noise associated with the physiologic-event-signal data by comparing each measured physiologic-event-signal datum with both the corresponding datum for the previously measured physiologic event, and the corresponding datum in the averaged-data template.
4. The artifact rejector of paragraph 3, further including a physiologic-event-noise monitor in communication with such physiologic-event-measuring equipment, and constructed to instruct such physiologic-event-measuring equipment during such measurement cycle to slow such physiologic-event-measurement rate if monitored noise exceeds a first preselected threshold.
5. The artifact rejector of paragraph 4, wherein the physiologic-event-noise monitor is also constructed to instruct such physiologic-event-measuring equipment during such measurement cycle based upon monitored noise exceeding a second preselected threshold, to stop for a preselected time period from proceeding to a next decreasing pressure and, during the preselected time period, to take a preselected number of additional physiologic-event measurements.
6. The artifact rejector of paragraph 5, wherein the physiologic-event-noise monitor is also constructed to instruct such physiologic-event-measuring equipment during such measurement cycle based upon monitored noise being below a third preselected threshold, to continue such measurement cycle at a preselected rate.
7. The artifact rejector of paragraph 6, wherein the physiologic-event-signal averager includes a sharp roll-off, low pass filter.
8. The artifact rejector of paragraph 7, wherein the filter is adjusted based upon the physiologic-event-measurement-cycle rate as a way of promoting accurate measurement of physiologic-event parameters by such physiologic-event-measuring equipment.
9. The artifact rejector of paragraph 8, wherein the filter is chosen from the group consisting essentially of a fourth-order Bessel filter, two cascaded, identical second-order Bessel filters, an elliptic filter, a Tchetschebyscheff filter, or finite impulse response filters.
10. The artifact rejector of paragraph 1, wherein the heart-beat-related signal is an ECG signal.
11. The artifact rejector of paragraph 10, further being constructed to instruct such physiologic-event-measuring equipment to save for a preselected time period the repetitive averaged physiologic-event-signal data, and further including a timing monitor in communication with such physiologic-event-measuring equipment and constructed to instruct such physiologic-event-measuring equipment during such measurement cycle to analyze the saved averaged physiologic-event-signal data if monitored time between corresponding physiologic-event signals and heart-beat-related signals exceeds a first preselected time threshold.
12. The artifact rejector of paragraph 11, wherein the timing monitor instructs such physiologic-event-measuring equipment to analyze the saved averaged physiologic-event-signal data by choosing as the next physiologic-event-oscillometric-signal datum the largest datum.
13. A artifact rejector for repetitive NIBP-oscillometric-signal data generated from electronically-controlled oscillometric-NIBP-measuring equipment, which equipment also generates repetitive heart-beat-related-signal data during an NIBP-measurement cycle that is characterized as measuring desired NIBP parameters by monitoring the repetitive NIBP-oscillometric-signal data corresponding to measured NIBP pulses at decreasing pressures according to an NIBP-measurement-cycle rate, comprising:
    an NIBP-oscillometric-signal averager in communication with such NIBP-measuring equipment, and constructed to generate repetitive averaged NIBP-oscillometric-signal data based upon a substantially stable time relationship between corresponding NIBP-oscillometric-signal data and heart-beat-related-signal data, with the repetitive averaged NIBP-oscillometric-signal data including less noise than the repetitive NIBP-oscillometric-signal data.
14. The artifact rejector of paragraph 13, wherein the NIBP-oscillometric-signal averager is constructed to generate and continuously update an averaged-data template by storing such repetitive averaged NIBP-oscillometric-signal data for a number of measured NIBP pulses.
15. The artifact rejector of paragraph 14, further including an NIBP-noise estimator in communication with such NIBP-oscillometric-measuring equipment, and constructed to estimate noise associated with the NIBP-oscillometric-signal data by comparing each measured NIBP-oscillometric-signal datum with both the corresponding datum for the previously measured NIBP pulse, and the corresponding datum in the averaged-data template.
16. The artifact rejector of paragraph 15, further including an NIBP-noise monitor in communication with such NIBP-measuring equipment, and constructed to instruct such NIBP-measuring equipment during such measurement cycle to slow cuff-bleed rate if monitored noise exceeds a first preselected threshold.
17. The artifact rejector of paragraph 16, wherein the NIBP-noise monitor is also constructed to instruct such NIBP-measuring equipment during such measurement cycle based upon monitored noise exceeding a second preselected threshold, to stop the cuff-bleed rate for a preselected time period and, during the preselected time period, to take additional NIBP-pulse measurements.

18. The artifact rejector of paragraph 17, wherein the NIBP-noise monitor is also constructed to instruct such NIBP-measuring equipment during such measurement cycle based upon monitored noise being below a third preselected threshold, to continue such measurement cycle at a preselected rate.

19. The artifact rejector of paragraph 18, wherein the NIBP-oscillometric-signal averager includes a sharp roll-off, low pass filter.

20. The artifact rejector of paragraph 19, wherein the filter is adjusted based upon the NIBP-measurement-cycle rate as a way of promoting accurate measurement of NIBP parameters by such NIBP-measuring equipment.

21. The artifact rejector of paragraph 20, wherein the filter is chosen from the group consisting essentially of a fourth-order Bessel filter, two cascaded, identical second-order Bessel filters, an elliptic filter, a Tchetschebyscheff filter, or finite impulse response filters.

22. The artifact rejector of paragraph 13, wherein the heart-beat-related signal is an ECG signal.

23. The artifact rejector of paragraph 21, further being constructed to instruct such NIBP-measuring equipment to save for a preselected time period the repetitive averaged NIBP-oscillometric-signal data, and further including a timing monitor in communication with such NIBP-measuring equipment and constructed to instruct such NIBP-measuring equipment during such measurement cycle to analyze the saved averaged NIBP-oscillometric-signal data if monitored time between corresponding NIBP-oscillometric signals and heart-beat-related signals exceeds a first preselected time threshold.

24. The artifact rejector of paragraph 23, wherein the timing monitor instructs such NIBP-measuring equipment to analyze the saved, averaged NIBP-oscillometric-signal data by choosing as the next NIBP-oscillometric-signal datum the largest datum.

25. An artifact rejection method for repetitive physiologic-event-signal data generated from physiologic-event-measuring equipment, which equipment also generates repetitive heart-beat-related-signal data during a physiologic-event measurement cycle, comprising:
    generating and storing repetitive averaged, physiologic-event-signal data based upon a time relationship between corresponding physiologic-event-signal data and heart-beat-related-signal data, with the repetitive averaged physiologic-event-signal data including less noise than the repetitive physiologic-event-signal data.

26. The artifact rejection method of paragraph 25, wherein the averaging includes the steps of generating and continuously updating an averaged-data template by storing such repetitive averaged physiologic-event-signal data for a preselected number of measured physiologic events.

27. The artifact rejection method of paragraph 26, further including the step of estimating physiologic-event-noise associated with the physiologic-event-signal data by comparing each measured physiologic-event-signal datum with both the corresponding datum for the previously measured physiologic event, and the corresponding datum in the averaged-data template.

28. The artifact rejection method of paragraph 27, further including the steps of monitoring the physiologic-event-noise and instructing such physiologic-event-measuring equipment during such measurement cycle to slow cuff-bleedrate if monitored noise exceeds a first preselected threshold.

29. The artifact rejection method of paragraph 28, wherein the monitoring further includes the steps of instructing such physiologic-event-measuring equipment during such measurement cycle based upon monitored noise exceeding a second preselected threshold, to stop the cuff-bleed rate for a preselected time period and, during the preselected time period, to take additional physiologic-event measurements.

30. The artifact rejection method of paragraph 29, wherein the monitoring further includes instructing such physiologic-event-measuring equipment during such measurement cycle based upon monitored noise being below a third preselected threshold, to continue such measurement cycle at a preselected rate.

31. The artifact rejection method of paragraph 30, wherein the averaging includes filtering the physiologic-event-signal data.

32. The artifact rejection method of paragraph 31, further including the step of adjusting the filter based upon the physiologic-event-measurement-cycle rate as a way of promoting accurate measurement of physiologic-event parameters by such physiologic-event-measuring equipment.

33. The artifact rejection method of paragraph 32, further including the steps of instructing such physiologic-event-measuring equipment to save for a preselected time period the repetitive averaged physiologic-event-signal data, monitoring the time between corresponding physiologic-event signals and heart-beat-related signals, and instructing such physiologic-event-measuring equipment during such measurement cycle to analyze the saved averaged physiologic-event-signal data if monitored time between corresponding physiologic-event signals and heart-beat-related signals exceeds a first preselected time threshold.

34. The artifact rejection method of paragraph 33, wherein the analyzing includes instructing such physiologic-event-measuring equipment to choose as the next physiologic-event-oscillometric-signal datum the largest datum.

We claim:

1. An artifact rejector for repetitive physiologic-event-signal data generated from physiologic-event-measuring equipment, which equipment also generates repetitive heart-beat-related-signal data during a physiologic-event measurement cycle, comprising:
    physiologic-event-measuring equipment constructed to measure physiologic events of a patient, the equipment also being constructed to generate repetitive physiologic-event signal data and heart-beat-related signal data during a physiologic-event measurement cycle;
    a physiologic-event-signal averager in communication with the physiologic-event-measuring equipment, and constructed to generate and store repetitive averaged physiologic-event-signal data based upon a substantially stable time relationship between corresponding repetitive physiologic-event-signal data and heart-beat-related-signal data, wherein the repetitive averaged physiologic-event-signal data includes less noise than the repetitive physiologic-event-signal data, and constructed to generate and continuously update an averaged-data template by storing the repetitive averaged physiologic-event-signal data monitored for a preselected time interval after an occurrence of the heart-beat-related signal; and wherein the physiologic-event-signal averager also includes a sharp roll-off, low pass filter, and wherein the averager is constructed to adjust the filter based upon the physiologic-event-measurement cycle as a way of promoting accurate measurement of physiologic-event parameters by the physiologic-event-measuring equipment.

2. The artifact rejector of claim 1, wherein the filter is chosen from the group consisting of a fourth-order Bessel filter, two cascaded, identical second-order Bessel filters, an elliptic filter, a Tchetschebyscheff filter, or finite impulse response filters.

3. An artifact rejector for repetitive NIBP-oscillometric-signal data generated from electronically-controlled oscillometric-NIBP-measuring equipment, which equipment also generates repetitive heart-beat-related-signal data during an NIBP-measurement cycle that is characterized as measuring desired NIBP parameters by monitoring the repetitive NIBP-oscillometric-signal data corresponding to measured NIBP pulses at decreasing pressures according to an NIBP-measurement cycle, comprising:

electronically-controlled oscillometric-NIBP-measuring equipment constructed to measure blood pressure of a patient, the equipment being constructed to generate repetitive NIBP-oscillometric-signal data and repetitive heat-beat-related signal data during an NIBP-measurement cycle that is characterized as measuring desired NIBP parameters by monitoring the repetitive NIBP-oscillometric signal data corresponding to measured NIBP pulses at decreasing pressures according to an NIBP-measurement-cycle rate;

an NIBP-oscillometric-signal averager in communication with the NIBP-measuring equipment, and constructed to generate repetitive averaged NIBP-oscillometric-signal data based upon a substantially stable time relationship between corresponding NIMP-oscillometric-signal data and heart-beat-related-signal data, wherein the repetitive averaged NIBP-oscillometric-signal data includes less noise than the repetitive NIBP-oscillometric-signal data, and constructed to generate and continuously update an averaged-data template by storing the repetitive averaged NIBP-oscillometric-signal data for a number of measured NIBP pulses; and wherein the NIBP-oscillometric-signal averager includes a sharp roll-off, low pass filter.

4. The artifact rejector of claim 3, wherein the NIBP-oscillometric-signal averager is constructed to adjust the filter based upon the NIBP-measurement-cycle rate as a way of promoting accurate measurement of NIBP parameters by such NIBP-measuring equipment.

5. The artifact rejector of claim 4, wherein the filter is chosen from the group consisting of a fourth-order Bessel filter, two cascaded, identical second-order Bessel filters, an elliptic filter, a Tchetschebyscheff filter, or finite impulse response filters.

* * * * *